United States Patent [19]
Schäfer et al.

[11] Patent Number: 6,078,049
[45] Date of Patent: Jun. 20, 2000

[54] STABLE ISOTOPE ANALYZER

[75] Inventors: Frank Schäfer, Bremen; Stefan Meier, Köln, both of Germany

[73] Assignee: EMG Elektronik Mechanik Geratebau GmbH, Bremen, Germany

[21] Appl. No.: 09/051,811

[22] PCT Filed: Oct. 9, 1996

[86] PCT No.: PCT/EP96/04384

§ 371 Date: Aug. 24, 1998

§ 102(e) Date: Aug. 24, 1998

[87] PCT Pub. No.: WO97/14952

PCT Pub. Date: Apr. 24, 1997

[30] Foreign Application Priority Data

Oct. 16, 1995 [DE] Germany .................. 195 38 4318

[51] Int. Cl.⁷ .................................................. G01N 21/31
[52] U.S. Cl. ............................... 250/339.09; 250/339.13; 250/345
[58] Field of Search ........................... 250/252.1, 339.09, 250/339.13, 345

[56] References Cited

U.S. PATENT DOCUMENTS

| | | |
|---|---|---|
| 5,077,469 | 12/1991 | Fabinski et al. . |
| 5,146,294 | 9/1992 | Grisar et al. .............................. 250/345 |
| 5,486,699 | 1/1996 | Fabinski et al. . |
| 5,747,809 | 5/1998 | Eckstrom ................................. 250/345 |

FOREIGN PATENT DOCUMENTS

| | | |
|---|---|---|
| 584 897A1 | 3/1994 | European Pat. Off. . |
| 3932838 A1 | 4/1991 | Germany . |
| 59-20837 | 2/1984 | Japan ...................................... 250/345 |

*Primary Examiner*—Constantine Hannaher
*Assistant Examiner*—Andrew Israel
*Attorney, Agent, or Firm*—Fay, Sharpe, Fagan, Minnich & McKee, LLP

[57] ABSTRACT

A stable isotope analyzer is concentration calibrated by measuring relative proportions of isotopes in a measurement gas. The measurement gas is a component of a gaseous mixture consisting of the measurement gas and one other gas or a mixture of gases containing none of the measurement gas. First, a mixture is produced with a relatively high concentration of the measurement gas and known isotope proportions. The concentration of the measurement gas in the other gas is determined and the isotope proportion is measured to determine a point on a calibration curve (measured isotope proportion values vs. measured concentration values). At least one further point on the calibration curve is determined by diluting the measurement gas in the mixture by introducing a gas or gaseous mixture containing no measurement gas. The reduced concentration is determined and the isotope proportion measured to determine another point on the calibration curve. The steps of reducing the measurement gas concentration in the gaseous mixture, measuring the measurement gas concentration, and measuring the isotope proportion are preferably repeated a plurality of times to plot the calibration curve more accurately.

14 Claims, 2 Drawing Sheets

STABLE ISOTOPE ANALYZER

BACKGROUND OF THE INVENTION

The invention relates to a method of concentration calibration of a stable isotope analyzer and to a stable isotope analyzer with means for concentration calibration.

In many fields of science (archeology, biology, geology, medicine, physiology, pharmacology) growing significance is attributed to the determination of isotope proportions. This applies primarily to the measurement of the $13CO_2/12CO_2$ ratio in the $CO_2$ of the respiratory gas, which provides valuable information with respect to diagnostic queries. Stable isotope analyzers permit the performance of measurements of the isotope proportion, for example determination of the selective isotope proportion ($*A_x, B_y$) in a measurement gas ($A_x, B_y$) or the determination of the ratio at which the isotope proportions exists. When measuring the 13C/12C ratio, specifically in a respiratory gas stable isotope diagnostic, specification of the so-called Delta-value has found acceptance, where a measured relative value is related to a standard ratio.

With the aid of non-disperse infra-red spectroscopy, a method is known for selective determination of an isotope proportion of a measurement gas (EP-A-584 897). The appliance described by way of exemplary embodiment serves for measuring the $13CO_2/12CO_2$ ratio.

It comprises two ray paths or analyzers, one of which serves for measuring the $13CO_2$-proportion and the other for measuring the $12CO_2$-proportion.

When taking isotope proportion measurements, it has come to light that the result depends upon the concentration in which the measurement gas is present in another gas (for example $CO_2$ in an inert gas) or a mixture of gas (for example $CO_2$ in air). In order to obtain measuring results not subject to said dependence, it is necessary to undertake a concentration calibration, prior to taking measurements.

In the appliance according to EP-A-584 897, calibration of the analyzer is done with the aid of calibration cells, which can—inserted behind the measuring cells—be pivoted into the respective ray path. The calibration cells are filled with a mixture of an inert gas and the isotope-free measurement gas proportion belonging to the respective path of rays. $CO_2$-free air flows through the measuring cells during calibration.

In order to perform a concentration-calibration with an appliance of this type, a plurality of calibration cells must first be made available with different concentrations of isotope-free portions of the measurement gas in an inert gas. These must be pivoted, successively, into the ray paths and, after completion of taking the concentration measurement, must again be tilted out. From the plurality of the individual concentration measurements, which are respectively required for each ray path, it is possible to determine the dependence of the isotope portions measurements on the concentration in the inert gas.

The concentration calibration can also be performed without any mechanical pivoting of the appropriate calibration cells. In such case, however, one proceeds from the premise that the course of the signals is similar to the concentration for each of the two isotope proportions, and that there will be no error or only negligible errors in establishing the ratio.

It has be determined in actual practice that such an assumption is justified with respect to the accuracy of the measurements that need to be obtained. For this type of calibration, a series of gas test samples must be made available and successively measured, with varying and correspondingly closely graduated $CO_2$-concentrations and a constant Delta-value.

It is the object of the present invention to significantly simplify the concentration calibration of a stable isotope analyzer.

This object is solved according to the invention by the identifying characteristics of the Patent Claims.

SUMMARY OF THE INVENTION

In accordance with one aspect of the present invention, a method for calibration of a stable isotope analyzer for isotope proportion measurements in a measurement gas is provided.

In accordance with another aspect of the present invention, a stable isotope analyzer is provided. The analyzer includes first and second measuring cells, a conveyor pump, and a line connection between the second cell and the conveyor pump.

One advantage of the present invention is that calibration of a stable isotope analyzer is achieved rapidly and accurately.

Another advantage of the present invention is that calibration is achieved with a single calibration sample of known Delta-value.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components and the various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
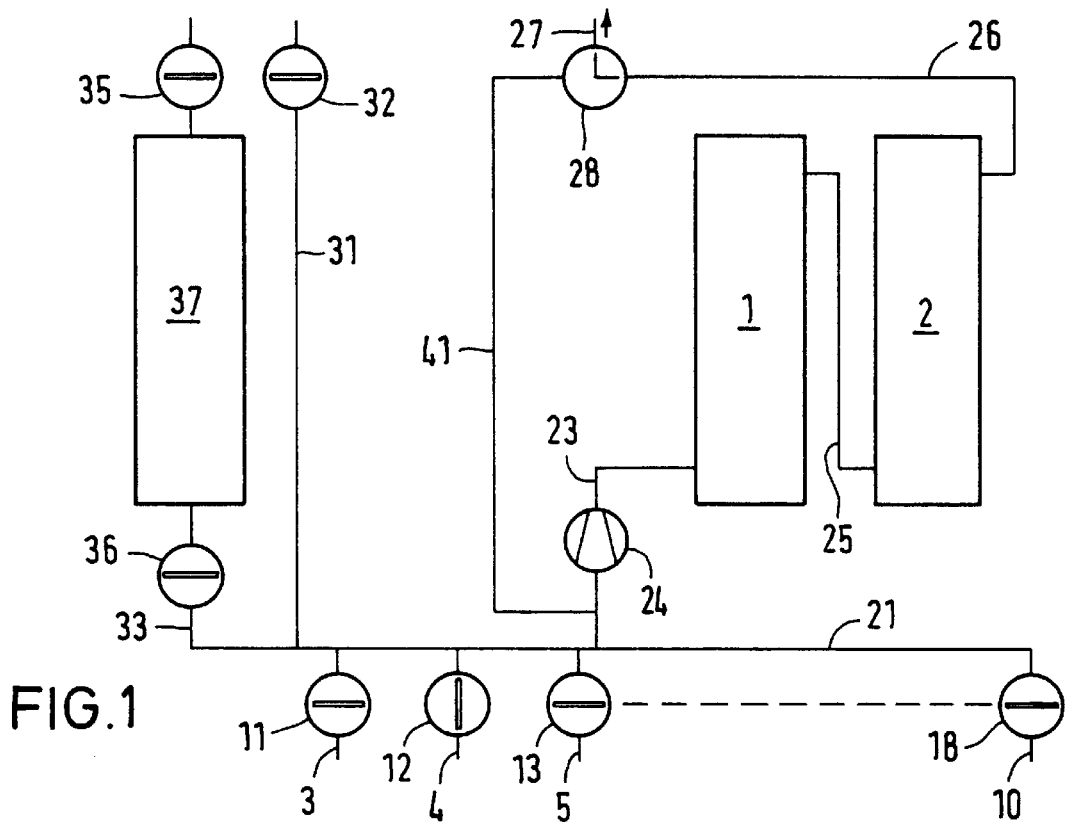
FIG. 1 is a schematic diagram of a stable isotope analyzer in the measurement phase, according to the present invention.

Based on the proposed measures, it is possible to eliminate the preparation of a plurality of test samples with varying $CO_2$-concentrations and constant Delta values in a gas mixture. This applies as well with respect to the mechanical appliances by which the plurality of test samples must be pivoted, in succession, into the two paths of the rays. The only requirement is that one gas mixture be prepared, having a relatively high $CO_2$-concentration and a known Delta-value. This means, that the concentration of the measurement gas in the test sample should lie at the upper limit of the range in which the measurement concentration normally lies.

If a non-disperse infra-red spectrometer is employed for performance of the isotope proportion measurements, having measuring cells which facilitate selective determination of isotope proportions, then the instrument can also be utilized for measurement of concentration required for calibration. The course of these concentration measurements is almost identical with the course of the isotope proportion measurements, so that the instrument itself need undergo only minor modifications in order to be able to execute concentration calibrations quickly, reliably and with precision. The possibility exists for automation, so that no specially trained personnel is needed to operate the instrument. Additional benefits and details of the invention are explained more specifically based on the exemplary embodiments depicted in FIGS. 1 to 4.

The Figures show, in highly diagrammatic view, the gas control in an infra-red stable isotope analyzer. The analyzer comprises two measuring cells 1 and 2, and also eight connection stubs 3 to 10 with electro-magnetically actuable valves 11 to 18. The connection stubs end in a line 21, which communicates via line 23 by conveyor pump 24 with the first measuring cell 1. The measuring cells 1 and 2 are connected by the line segment 25 such that during the measurement phase the measuring gas flows successively through the measuring cells. Measuring cell 2 is connected with line 26, via which the measuring gas flows to the outlet 27, which is formed in the depicted exemplary embodiment by a 3/2-way-valve 28.

Into line 21 also issues air supply line 31 with valve 32. In addition, $CO_2$-free air may be supplied to line 21. To that end, line 33 is provided with valves 35 and 36 and also with a cartridge 37 in which is located an adsorption medium for $CO_2$, for example soda lime.

FIG. 1 represents the position of the valves in a measurement phase in which measuring gas flows in via the connection stub 4. In a respiratory gas analysis, for example, eight respiratory gas bags are connected to connection stubs 3 to 10, which are successively connected with measuring cells 1 and 2. A purging period is inserted before each measurement taking, during which the entire ray path is purged with air. The valves of the respiratory air bags are closed and only the "air" line 31 is open. Subsequently, the "air" line 31 is closed again and valve 12, located in front of the to be measured respiratory air bag, is opened. Before the start of the measurement taking, during the "waiting period" (length approximately 30 seconds) the entire volume (lines, measuring cells) is flooded with respiratory air. Subsequent thereto, the measurement is executed under constant continued pumping. Once the bag has been measured, the instrument automatically—controlled by a computer—switches over to the next respiratory bag and the operation continues.

Figure 2:
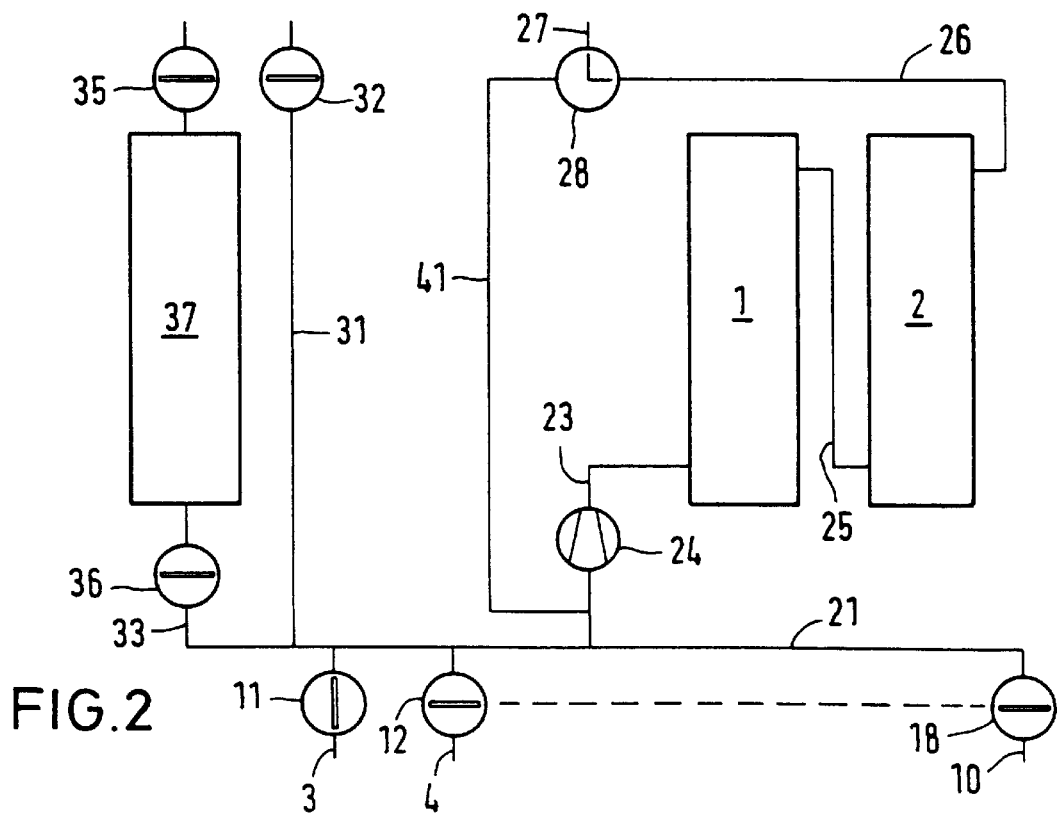
FIG. 2 is a schematic diagram of the stable isotope analyzer of FIG. 1 with valve 11 open to admit respiratory air.
Figure 3:
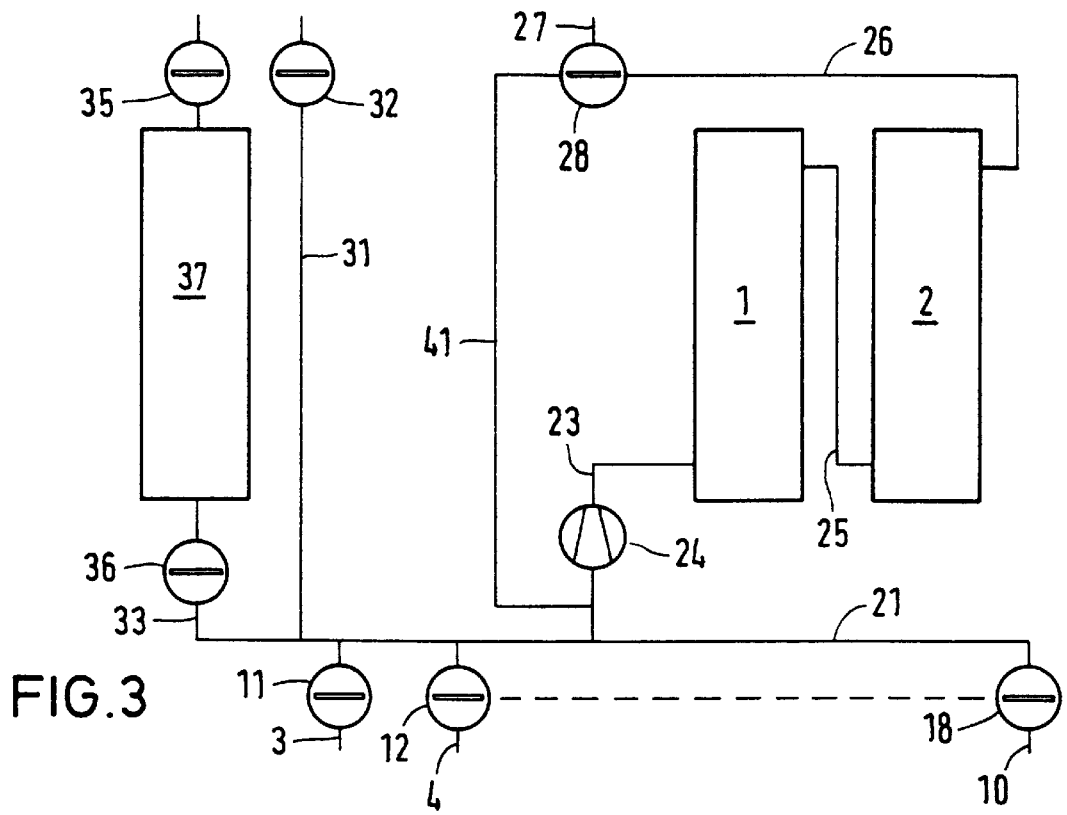
FIG. 3 is a schematic diagram of the stable isotope analyzer of FIG. 1 during circulation of respiratory air.
Figure 4:
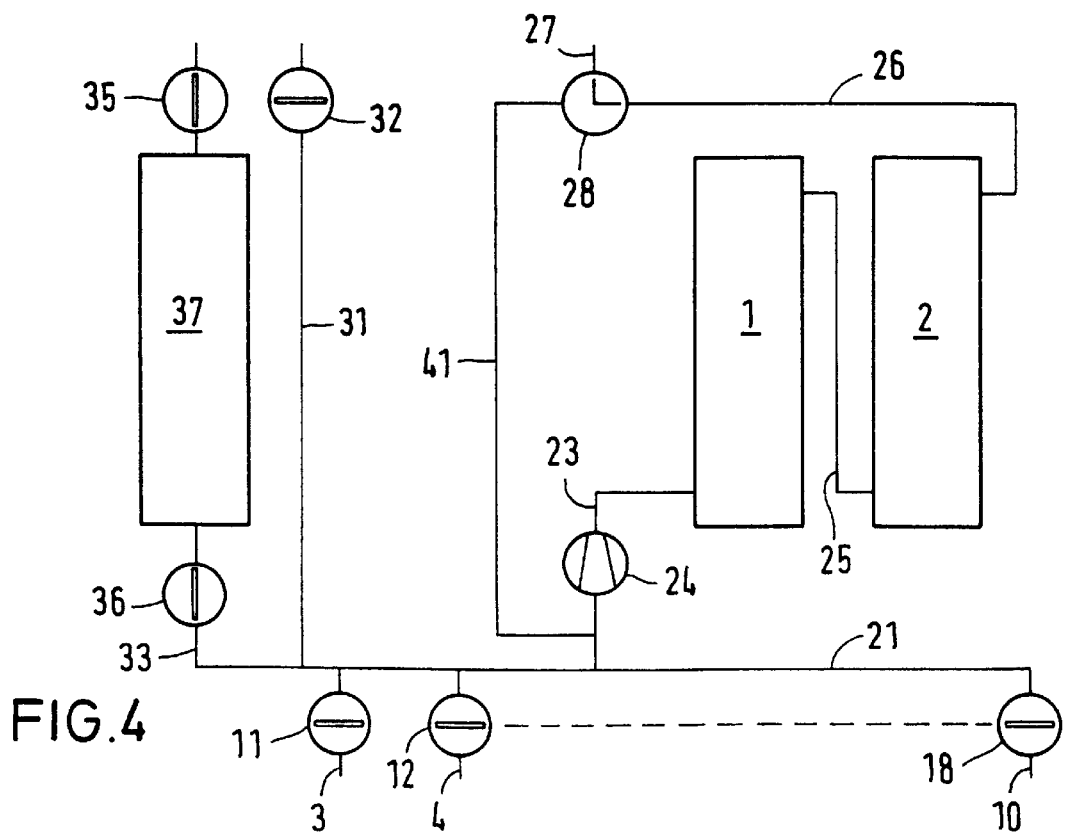
FIG. 4 is a schematic diagram of the stable isotope analyzer of FIG. 1 with the valve positions adjusted for the short-term inflow of $CO_2$-free air.

Execution of a concentration calibration in respiratory analysis is going to be explained by means of FIGS. 2–4. Connected to connection stub 3 is a respiratory air bag containing respiratory air with relatively high $CO_2$-concentration. Said test sample can, for example, be prepared in that a respiratory air bag is filled by exhalation from a person who held his/her breath for a short period of time. Prior to calibration, the entire volume is purged with $CO_2$-free air and subsequently valve 11 is opened. After flooding the entire volume with respiratory air, valve 11 is closed and valve 28 brought into a position in which the respiratory air is circulated (compare FIG. 3). For that purpose, line segment 41 is provided, which connects valve 28 with the inlet of conveyor pump 24. With the aid of measuring cells 1 and/or 2, the absolute $CO_2$-concentration is measured during this phase and the Delta-Value ascertained. From these measurements, a point is established in the system of coordinates for the calibration curve (Delta Value versus concentration). In order to determine another point of the calibration curve, the respiratory gas which is located in the system is diluted with $CO_2$-free air, so that there is a reduction in the $CO_2$-concentration. FIG. 4 depicts the valve positions needed during the short-term inflow of $CO_2$-free air. Valves 35, 36 are in open position. A part of the circulated gas flows out via valve 28. Subsequently, the valves are again positioned according to FIG. 3 and the steps "measurement of concentration" and "measurement of Delta-Value" are repeated. This results in obtaining another point on the calibration curve, The desired calibration curve is obtained by means of additional, gradual dilution of gas within the system and repeated measurement-taking. The degree of concentration modification is adjusted via chronologically regulated opening of valves 35 and 36.

The represented appliance also permits calibration of the zero point. It is the purpose of said calibration to set to "0" the measurement value of the $CO_2$-concentration, read by the instrument, when the air that is totally devoid of $CO_2$. For that purpose, the instrument is supplied with air via cartridge 37, containing soda lime, which chemically binds the $CO_2$.

When required, measurement taking is automatic and lasts until the measured value no longer shows fluctuations. The instrument is then set to "0" per internal command.

It is fundamental, however, that the invention facilitates the execution of a concentration calibration with an only slightly modified stable isotope analyzer, which is simple, reliable and precise. Because of the possibility of automating the measurement taking and also the calibration course, the sequences can be regulated by computer. It is appropriate to enter the calibration curve into the memory bank so that comparison with the calibration curve of the Delta-values measured on additional respiratory gas samples can likewise be automated.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for concentration calibration of a stable isotope analyzer employed for isotope proportion measurements in a measurement gas, wherein the measurement gas is a component of a gas mixture which consists of the measurement gas and an additional gas, the additional gas being devoid of the measurement gas and the gas mixture, the method including:

preparing the gas mixture by mixing the measuring gas and the additional gas, which gas mixture has a relatively high measurement gas concentration and known isotope proportions;

determining a first point on a calibration curve of isotope proportions versus concentration measurement values, the determining of the point including:
  determining a first concentration of the measurement gas in the gas mixture, and
  measuring a first isotope proportion in the gas mixture;
determining another point on the calibration curve by:
  reducing the concentration of the measurement gas in the gas mixture by supplying a gas devoid of the measurement gas and the gas mixture, determining another concentration of the measurement gas in the gas mixture, and measuring another isotope proportion in the gas mixture;

repeating the steps of reducing the concentration of the measurement gas in the gas mixture, determining another concentration of the measurement gas, and measuring another isotope proportion a plurality of times to produce a calibration curve.

2. The method according to claim 1, carrying out the measurement case concentration determining steps with a measuring instrument which is present in the stable isotope analyzer.

3. The method according to claim 1 wherein:

the isotope proportions are measured with a non-disperse infra-red spectrometer with two measuring cells for selective determination of the isotope proportions;

and the gas mixture concentrations are determined with at least one of the measuring cells.

4. The method according to claim 3, wherein the gas mixture concentration is determined with a first of the measuring cells which a proportion of a predominantly occurring isotope.

5. The method according to claim 3, wherein the measurement gas is circulated via the measuring cells during the calibration.

6. The method according to claim 1, wherein the measurement gas is $CO_2$, wherein the steps of measuring the first and another isotope proportions measures absolute concentrations of $CO_2$ isotopes, and further including:

determining a Delta-value from the absolute concentrations of the $CO_2$ isotopes.

7. The method according to claim 5, wherein the analyzer serves for performing $CO_2$-isotope proportion measurements in respiratory gas, and wherein the step of preparing the gas mixture with the relatively high measurement gas concentration includes filling a respiratory bag by exhalation from a person who has held a breath for a short period of time.

8. A stable isotope analyzer including:

a first measuring cell and a second measuring cell for execution of isotope proportion measurements, the first measuring cell having a first measuring cell inlet and a first measuring cell exit, the second measuring cell having a second measuring cell inlet and a second measuring cell exit, the second measuring cell inlet being connected with the first measuring cell exit such that the second measuring cell receives a gas which has flowed through the first measuring cell;

a conveyor pump having an intake and a conveyor pump exit;

a first line connection between the second measuring cell exit and the conveyor pump intake; and, a second line connection between the conveyor pump exit and the first measuring cell inlet.

9. The analyzer according to claim 8, wherein a 3/2-way valve is located in the first line connection for selectively connecting the second measuring cell exit with a gas outlet and with the conveyor pump intake.

10. A method for determining isotope proportions in a measuring gas which includes a first stable isotope and a second stable isotope, proportions of the first stable isotope and second stable isotope in the measuring gas varying with a concentration of the measuring gas in a mixture consisting of the measuring gas and a second gas, the method comprising:

a) introducing a calibration sample into an analyzer, the calibration sample including the measuring gas with a known initial proportion of the first stable isotope and the second stable isotope;

b) determining a concentration of the measuring gas in the calibration sample;

c) measuring a proportion of the first stable isotope relative to the second stable isotope in the calibration sample;

d) diluting the calibration sample with a diluting gas to reduce the concentration of the measuring gas, the diluting gas being substantially free of the measuring gas;

e) repeating steps (b) through (d) to obtain a calibration curve of the isotope proportion versus the concentration of the measuring gas in the analyzer;

f) purging the analyzer to remove the calibration sample from the analyzer;

g) introducing a sample to be tested into the analyzer, the sample to be tested containing the measuring gas;

h) determining a concentration of the measuring gas in the sample to be tested;

i) determining the proportion of the first and stable isotopes in the sample to be tested; and, j) correcting the proportion measured for the sample with the calibration curve.

11. The method according to claim 10, wherein the sample to be treated includes air exhaled from a person who has held their breath for a short period of time and the measuring gas is carbon dioxide.

12. The method according to claim 11, wherein the diluting gas includes air from which carbon dioxide has been removed.

13. A method for concentration calibration of a stable isotope comprising:

determining a first concentration of a measurement gas in a gas mixture;

reducing the concentration of the measurement gas in the gas mixture by supplying a gas devoid of the measurement gas and the gas mixture;

determining the reduced concentration of the measurement gas in the gas mixture.

14. The method as set forth in claim 13 further including:

from the determined first and reduced concentrations, determining a calibration curve.

* * * * *